United States Patent
Harms et al.

[11] Patent Number: 5,873,878
[45] Date of Patent: Feb. 23, 1999

[54] ANCHORING MEMBER

[76] Inventors: Jürgen Harms, Vogesenstrasse 60, D-76337 Waldbronn; Lutz Biedermann, Am Schäfersteig 8, D-78048 VS-Villingen, both of Germany

[21] Appl. No.: 841,156

[22] Filed: Apr. 29, 1997

[30] Foreign Application Priority Data

Apr. 30, 1996 [DE] Germany ............... 196 17 362.0

[51] Int. Cl.⁶ .................................................. A61B 17/70
[52] U.S. Cl. ................................................ 606/61; 606/73
[58] Field of Search ........................ 606/61, 60, 72, 606/73; 623/17

[56] References Cited

U.S. PATENT DOCUMENTS

| 5,312,405 | 5/1994 | Korotko et al. | 606/61 |
| 5,380,326 | 1/1995 | Lin | 606/61 |
| 5,507,746 | 4/1996 | Lin | 606/61 |
| 5,630,817 | 5/1997 | Rokengem et al. | 606/61 |

FOREIGN PATENT DOCUMENTS

| 0 578 320 A1 | 5/1993 | European Pat. Off. |
| WO 93/11715 | 6/1993 | WIPO |
| WO 94/08527 | 4/1994 | WIPO |

*Primary Examiner*—Guy V. Tucker
*Attorney, Agent, or Firm*—George W. Neuner

[57] ABSTRACT

An anchoring member is provided with a shaft 2 for fastening to a bone and a head 3 for connection with a rod 10, the head being connected to the shaft and having a generally U-shaped cross-section with a base and two legs laterally defining a first channel for receiving the rod. The rod is retained in a desired position within the channel by a fastening member. In order to allow the anchoring member to be used not only with a rod of the appropriate diameter, but also with rods having smaller diameters the anchoring member comprises an insert member 13, 13' having a generally U-shaped cross-section forming a second channel 18 defined by its two free sides 14, 15 for receiving a rod 17 having a smaller diameter. The outer curvature of the U-shaped cross-section of the insert member 13, 13' is substantially equal to or slightly smaller than the internal curvature of the first channel 4.

19 Claims, 2 Drawing Sheets

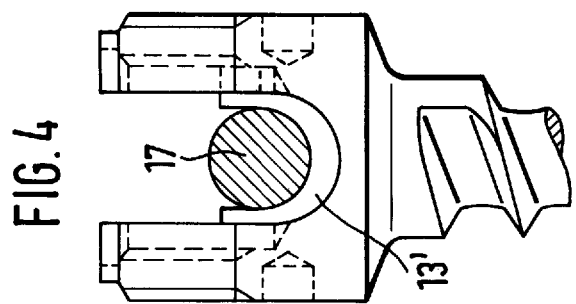
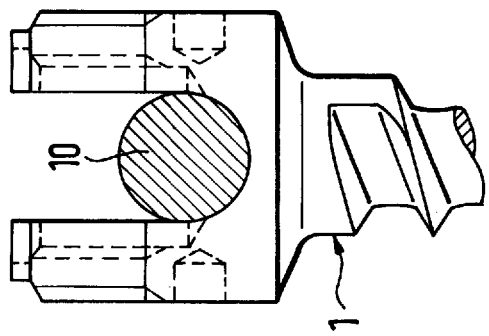
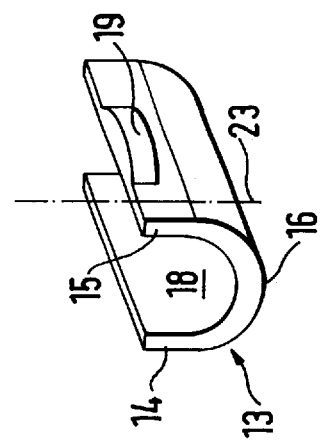
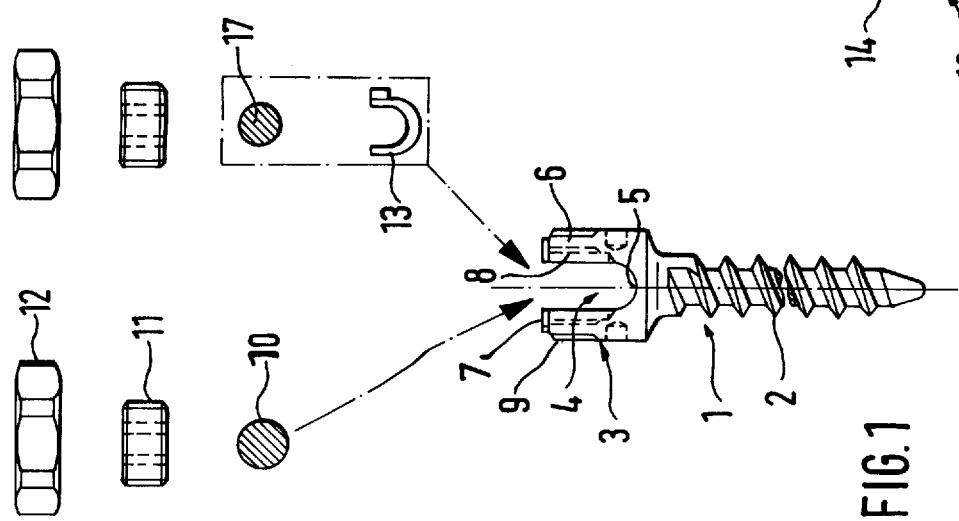

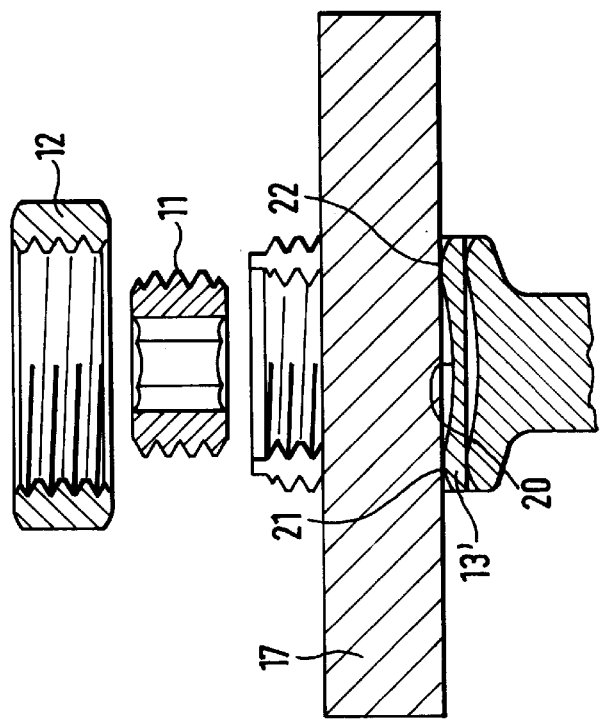
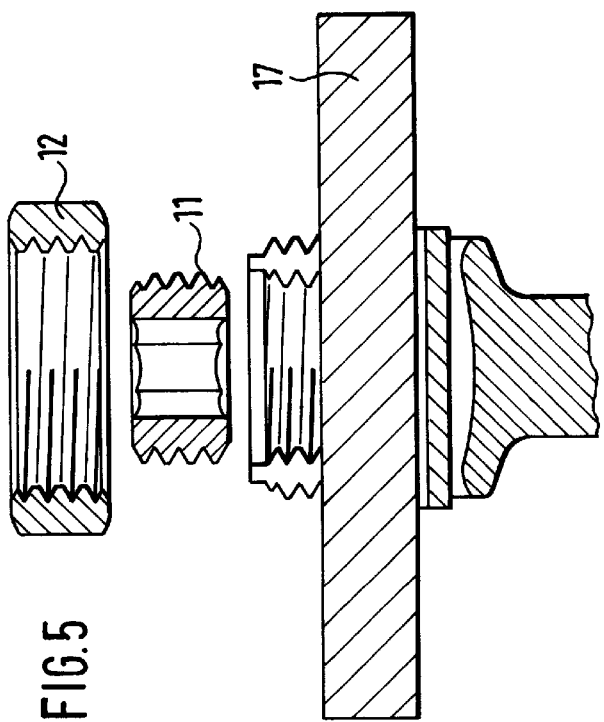
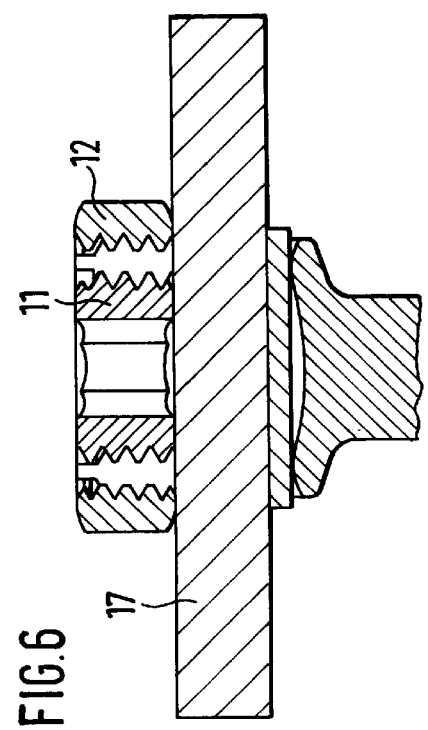

ANCHORING MEMBER

BACKGROUND OF THE INVENTION

The invention relates to an anchoring member for attachment to a vertebra and for connection with a first rod having a first diameter or a second rod having a second smaller diameter. The anchoring member comprises a shaft and a head for connection to the rods, the head being connected to the shaft and having a generally U-shaped cross-section with a curved base and two legs laterally defining a first channel for receiving the first or second rods and a center axis extending between the legs perpendicular to the base, a fastening member for cooperation with the legs to fasten the rods within the first channel and a cylindrical recess in said head being concentric to the center axis and extending from the free end of the legs to the base of the first channel.

Such an anchoring member is known from document WO 94/08527. The radius of the base of the U-shaped channel, which is substantially equal to half of the distance between the two legs, is chosen as a function of the diameter of the rod to be received so that the rod can be placed into the channel without getting jammed. The use of rods having different diameters requires corresponding different anchoring members having their radius of the U-shaped base adapted to the diameter of the rod. This not only increases the costs of stock-keeping, but also renders the operation proper more difficult.

Document WO 93/11715 discloses an anchoring member having a shaft to be fastened to a bone and a head for connection with a rod. The head has a generally U-shaped cross-section and two free legs defining a first channel for receiving the rod therein. In order to allow the use of rods having different diameters an insert member is provided with a generally U-shaped cross-section and a second channel defined by the two free legs thereof for receiving a rod having a smaller diameter. The length of the insert member is greater than the length of the first channel. Projections are provided at both opposite ends of the insert member and the distance between the projections is substantially equal to the length of the first channel. After insertion the two projections engage the outside of the head and thereby prevent the insert member from being relatively displaced within the channel during the adjustment operation. This changes the outer contour of the head.

It is the object of the invention to provide an anchoring member with an insert member which is formed so that the above disadvantage is avoided.

SUMMARY OF THE INVENTION

This object is achieved by providing an anchoring member comprising an insert member having a generally U-shaped cross-section with curved center portion and two sides defining a second channel for receiving the second rod, the curved center portion having an outer curvature which generally corresponds to a curvature of the curved base of the head or is slightly smaller, the insert member having at least one nose projecting from its outer surface. Thus, the outer contour of the head is not changed. The surgeon may therefore use a single formfitting tool for handling the anchoring member with or without insert member.

Further developments of the invention are defined in the subclaims.

BRIEF DESCRIPTION OF THE DRAWINGS

Further features and advantages of the invention will be apparent from the description of an embodiment with reference to the Figures. In the Figures:

FIG. 1 is a side view of a first embodiment of the anchoring member in exploded representation;

FIG. 2 is a perspective view of an insert member;

FIG. 3 is a side view of a portion with a rod having a first diameter being inserted;

FIG. 4 is a corresponding side view with a rod having a second diameter being inserted;

FIG. 5 is a sectional side view of a second embodiment of an anchoring member when taken apart;

FIG. 6 shows the same embodiment in assembled state; and

FIG. 7 is a sectional side view of a further modified embodiment.

DESCRIPTION OF THE PREFERRED EMBODIMENTS

The anchoring member own in FIG. 1 comprises a screw 1 to be introduced into a spinal column and having a threaded shaft 2 and a head 3. The head 3 comprises a U-shaped first channel 4 which is symmetric with respect to the central axis of the threaded shaft 2 and which has a base 5 directed towards the threaded shaft 2. The lateral wall of the head defining the U-shaped channel 4 is formed by free legs 6, 7. A bore having an internal thread 8 is concentric with the center axis of the threaded shaft 2 and provided in the interior of the channel which extends perpendicular to the U-shaped cross-section. The head itself is cylindrical and comprises an external thread 9 at the region of the free legs 6, 7.

A threaded screw 11 formed as a threaded bolt is provided for anchoring a rod 10 having a first diameter by means of the screw. The threaded screw 11 comprises an external thread cooperating with the internal thread 8 for screwing into the first channel 4. The threaded screw 11 has a concentric hexagon bore for engagement of a screw driver. Furthermore, a surrounding member embracing both U-shaped legs 6, 7 at their outer side is formed as a spigot 12 having a thread which cooperates with the external thread 9. As best shown in FIG. 3 the base 5 of the U-shaped first channel has a radius which is larger than the radius of the rod 10 to be received therein by such a slight amount only that the rod may easily be inserted into the U-shaped recess and removed therefrom resp., while being guided thereby. Both the internal thread 8 and the external thread 9 extend as far downwards, i.e. in direction towards the base 5, that the projection onto the center axis is spaced from the base 5 by a distance which is smaller than the diameter of the rod 10 to be received.

In the shown embodiment the anchoring member has a threaded shaft. It may also be formed as a hook instead. The hook as well serves for connection to a member of the spinal column, whereby the hook is introduced into the arc of a vertebra.

The anchoring member 1 additionally comprises a shell-type insert member 13. As best shown in FIGS. 1 and 2 the insert member 13 has a U-shaped cross-section with two parallel free sides 14, 15. The outer side of its base portion 16 has a radius which is substantially equal to the internal radius of the first channel 4 and smaller by such an amount that the insert member 13 can be inserted into the recess 4 and removed therefrom without getting jammed while being laterally guided by the U-shaped first channel. The insert member has a length measured in a direction perpendicular to the U-shaped cross-section thereof which is generally equal to the length of the first channel 4. The base of the insert member has an internal radius which substantially corresponds to the radius of a rod 17 to be received, the rod 17 having a smaller second diameter. The second channel 18 formed thereby is also defined by the inner surfaces of the parallel sides 14, 15. The distance between the sides 14, 15 and the internal radius of the base portion are designed to be generally equal to the diameter or radius, resp., of the rod 17 and correspond thereto so that the rod 17 can be inserted into the second channel 18 and removed therefrom without getting jammed while being laterally guided by the channel walls, as best shown in FIG. 4.

As best shown in FIG. 2 at least one of the free sides 14, 15 of the insert member 13 has a nose 19 projecting from the outer surface at the free end thereof. The nose is formed as an outwardly extending segment of a circle which lies in a plane perpendicular to the center axis of the U-shaped cross-section and has its center on the axis of symmetry 23 extending perpendicular from the base of the second channel. The radius of the segment is substantially equal to the radius of the bore comprising the internal thread 8 but smaller by just an amount such that the member can be placed into the interior of the second channel and removed therefrom without getting jammed. The nose 19 provides for a particularly simple handling in operation, because the insert member 13 is always in its correct position within the first channel 4. In the present case the nose 19 is formed as a segment of a circle. It is essential that its shape always corresponds to a lateral recess provided within the first channel 4 so that it engages this lateral recess in such a manner that the insert member is locked against movement in longitudinal direction of the channel 4.

It is clearly apparent from FIGS. 1 to 4 that one and the same anchoring member can be used in connection with a first rod 10 having a greater diameter and a second rod 11 having a smaller diameter.

The FIGS. 5 and 6 show an embodiment which differs from the first described embodiment merely in that the bottom of the first recess 4 has a camber towards its center with a depressed portion and outwardly tapering side portion on both sides. In this case the insert member 13 is inserted in the same manner as in the first embodiment.

In the embodiment shown in FIG. 7 the insert member 13' has a bottom with the base of the U-shaped channel having a curved portion in a direction perpendicular to the U-shaped cross-section, the curvature comprising a depressed center portion 20 and two convex portions 21, 22 spaced from the center. The spacing of each convex portion 21, 22 is substantially equal to the mean of the radius of the internal thread and the radius of the external thread.

In operation the surgeon uses one and the same screw or one and the same hook for the conventional rod 10 with the greater diameter. If he wishes to insert a smaller rod 17, he additionally applies the insert member 13 corresponding to the anchoring member and thereafter inserts the rod 17.

The rod 10 or 17, resp., is fastened in known manner. According to the embodiments an internal screw 11 and the spigot 12 are provided for this purpose. However, any other fixation can be used.

Although the invention has been described with reference to specific example embodiments, it is to be understood that it is intended to cover all modifications and equivalents within the scope of the appended claims.

What is claimed is:

1. An anchoring member for attachment to a vertebra and for use with a first rod having a first diameter and a second rod having a second smaller diameter, the anchoring member having a shaft and a head for connection to said rods, said head being connected to said shaft and having a generally U-shaped cross-section with a curved base and two legs laterally defining a first channel for receiving said first rod and a center axis extending between said legs perpendicular to said base, said anchoring member further comprising:

a fastening member for cooperation with said legs to fasten said rods within said first channel, a cylindrical recess in said head being concentric to said center axis and extending from the free end of said legs to said base of said first channel, and an insert member having a generally U-shaped cross-section with a curved center portion and two sides defining a second channel for receiving said second rod, said curved center portion having an outer curvature which generally corresponds to an inner curvature of said curved base of said head or is slightly smaller, said insert member having at least one nose projecting from its outer surface and engaging said recess.

2. The anchoring member of claim 1, wherein a length of said insert member measured in a direction perpendicular to said U-shaped cross-section substantially corresponds to a length of said first channel.

3. The anchoring member of claim 1, wherein said nose is provided substantially at the center of said sides at their upper edges in longitudinal direction of said insert member.

4. The anchoring member of claim 3, wherein said nose is substantially equal to or slightly smaller than the circle segment of the cylindrical recess adjacent to said side.

5. The anchoring member of claim 1, wherein said nose is formed at a free end of one of said sides.

6. The anchoring member of claim 5, wherein said nose is substantially equal to or slightly smaller than the circle segment of the cylindrical recess adjacent to said side.

7. The anchoring member of claim 1, wherein said base of said second channel has a curved portion in a direction perpendicular to the U-shaped cross-section.

8. The anchoring member of claim 7, wherein said curvature comprises a depressed portion towards the center and two projecting convex portions on opposing sides of the center and spaced therefrom.

9. The anchoring member of claim 8, wherein a distance of said convex portions from the center substantially corresponds to the middle between the radius of the internal thread and the radius of the external thread.

10. The anchoring member of claim 1, wherein said connection of said shaft and said head comprises an articulation.

11. Anchoring member for attachment to a vertebra and for use with a first rod having a first diameter and a second rod having a second smaller diameter, the anchoring member having a shaft and a head for connection to said rods, said head being connected to said shaft and having a generally U-shaped cross-section with a curved base and two legs laterally defining a first channel for receiving said first rod and a center axis extending between said legs perpendicular to said base, said anchoring member further comprising:

a fastening member for cooperation with said legs to fasten said rods within said first channel, a cylindrical recess in said head being concentric to said center axis and extending from the free end of said legs to said base of said first channel, and an insert member having a generally U-shaped cross-section with a curved center portion and two sides defining a second channel for receiving said second rod, said curved center portion having an outer curvature which generally corresponds to an inner curvature of said curved base of said head or is slightly smaller, said insert member having at least one nose projecting from its outer surface, wherein said nose is provided substantially at the center of said sides at their upper edges in longitudinal direction of said insert member.

12. The anchoring member of claim 11, wherein a length of said insert member measured in a direction perpendicular to said U-shaped cross-section substantially corresponds to a length of said first channel.

13. The anchoring member of claim 11, wherein said nose is formed at a free end of one of said sides.

14. The anchoring member of claim 13, wherein said nose is substantially equal to or slightly smaller than the circle segment of the cylindrical recess adjacent to said side.

15. The anchoring member of claim 11, wherein said nose is substantially equal to or slightly smaller than the circle segment of the cylindrical recess adjacent to said side.

16. The anchoring member of claim 11, wherein said base of said second channel has a curved portion in a direction perpendicular to the U-shaped cross-section.

17. The anchoring member of claim 16, wherein said curvature comprises a depressed portion towards the center and two projecting convex portions on opposing sides of the center and spaced therefrom.

18. The anchoring member of claim 17, wherein a distance of said convex portions from the center substantially corresponds to the middle between the radius of the internal thread and the radius of the external thread.

19. The anchoring member of claim 11, wherein said connection of said shaft and said head comprises an articulation.

* * * * *